(12) United States Patent
Sierra et al.

(10) Patent No.: US 7,278,293 B2
(45) Date of Patent: Oct. 9, 2007

(54) SUBMERSIBLE PROBE

(75) Inventors: Gabriel Lazaro Sierra, Minneapolis, MN (US); William Thomas Anderson, Chanhassen, MN (US); Edward Charles Hajek, Chaska, MN (US)

(73) Assignee: Rosemount, Inc., Eden Prairie, MN (US)

( * ) Notice: Subject to any disclaimer, the term of this patent is extended or adjusted under 35 U.S.C. 154(b) by 56 days.

(21) Appl. No.: 11/154,309

(22) Filed: Jun. 16, 2005

(65) Prior Publication Data

US 2006/0283238 A1    Dec. 21, 2006

(51) Int. Cl.
*G01N 11/00*    (2006.01)

(52) U.S. Cl. .......................... 73/53.01; 73/309
(58) Field of Classification Search ............. 73/290 R, 73/53.01, 305, 309, 54.02
See application file for complete search history.

(56) References Cited

U.S. PATENT DOCUMENTS

| | | | |
|---|---|---|---|
| 3,148,542 A * | 9/1964 | Clift, Jr. ..................... 73/313 |
| 3,670,575 A | 6/1972 | Emerick |
| 4,187,796 A * | 2/1980 | Ess ........................... 114/312 |
| 4,191,049 A * | 3/1980 | Bowditch et al. ........ 73/170.11 |
| 4,202,034 A * | 5/1980 | Bowditch et al. ............. 702/2 |
| 4,202,036 A * | 5/1980 | Bowditch et al. ............ 702/33 |
| 4,258,568 A | 3/1981 | Boetes et al. |
| 4,408,488 A | 10/1983 | Marshall |
| 4,777,819 A | 10/1988 | Hoyt et al. |
| 4,924,698 A * | 5/1990 | Echert et al. ............ 73/170.29 |
| 4,972,710 A | 11/1990 | Uhlarik et al. |
| 5,156,042 A | 10/1992 | Carlin et al. |
| 5,209,112 A | 5/1993 | McCoy et al. |
| 5,283,767 A * | 2/1994 | McCoy ......................... 367/4 |
| 5,379,267 A | 1/1995 | Sparks et al. |
| 5,400,651 A | 3/1995 | Welch |
| 5,457,990 A * | 10/1995 | Oswald et al. ............ 73/290 V |
| 5,469,749 A | 11/1995 | Shimada et al. |
| 5,496,136 A | 3/1996 | Egan |
| 5,708,424 A | 1/1998 | Orlando et al. |
| 5,950,487 A | 9/1999 | Maresca, Jr. et al. |
| 6,121,780 A | 9/2000 | Cruickshank et al. |
| 6,142,092 A * | 11/2000 | Coupland ................... 114/331 |
| 6,229,448 B1 | 5/2001 | Bennett, Jr. et al. |
| 6,335,690 B1 | 1/2002 | Konchin et al. |
| 6,369,715 B2 | 4/2002 | Bennett, Jr. et al. |
| 6,553,336 B1 | 4/2003 | Johnson et al. |
| 6,724,197 B2 | 4/2004 | Neven et al. |
| 6,772,705 B2 | 8/2004 | Leonard et al. |
| 6,807,856 B1 * | 10/2004 | Webb ...................... 73/170.29 |
| 6,951,131 B2 * | 10/2005 | Sawert et al. ............ 73/290 V |
| 2002/0170354 A1* | 11/2002 | Monsrud et al. ............. 73/305 |
| 2003/0029223 A1 | 2/2003 | Taylor, III et al. |

(Continued)

OTHER PUBLICATIONS

"Model 181KT—Miniature Depth Sensor." Available online, http://www.paroscientific.com/pdf/181KT.pdf, printed on Jul. 22, 2005.

*Primary Examiner*—Hezron Williams
*Assistant Examiner*—Rodney Frank
(74) *Attorney, Agent, or Firm*—Kinney & Lange, P.A.

(57) ABSTRACT

A probe for deployment in a fluid measures produces an output representative of a parameter associated with the fluid. The probe includes a density control system to control a density of the probe and a locating system to track a location of probe in the fluid.

25 Claims, 10 Drawing Sheets

U.S. PATENT DOCUMENTS

2004/0004545 A1 1/2004 Early
2004/0004550 A1 1/2004 Early
2004/0004551 A1 1/2004 Early

* cited by examiner

SUBMERSIBLE PROBE

BACKGROUND OF THE INVENTION

The present invention relates generally to submersible sensing systems. More specifically, the present invention relates to submersible probes for sensing parameters associated with fluids of fluid environments.

Various fluids are stored in above-ground or in-ground fluid storage tanks. For example, petroleum-based products such as fuel oil or gasoline are routinely stored in such tanks. A major concern for any industry in which fluids are stored in these tanks is the accurate control and inventorying of these fluids to address industry and safety requirements. This is especially true for industries that store combustible fluids such as fuel oil and gasoline. As such, there is a continuing need for more effective sensing strategies to meet the fluid monitoring needs of these industries.

In addition, there is also a continuing need for more effective sensing strategies to study the physical, biological, and geological properties of the world's oceans and freshwater bodies.

BRIEF SUMMARY OF THE INVENTION

The present invention includes a probe for deployment in a fluid and for producing an output representative of a parameter associated with the fluid. A density of the probe is changed to move the probe from a first location in the fluid to a second location in the fluid. Movement of the probe is tracked using a locating system carried by the probe.

DETAILED DESCRIPTION

Figure 1:
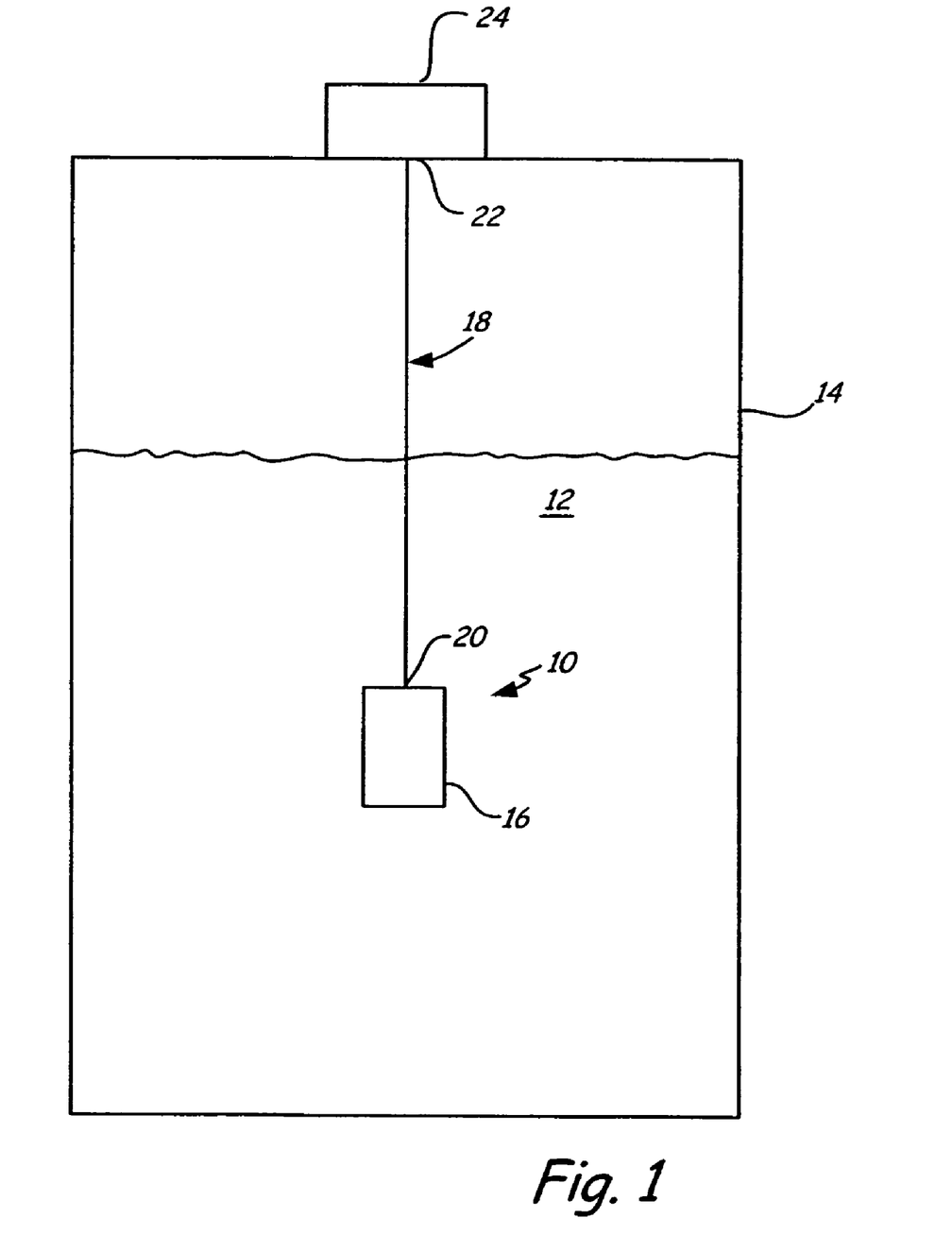
FIG. 1 depicts a submersible probe of the present invention deployed in a fluid of a fluid storage tank.

FIG. 1 shows submersible probe 10 of the present invention deployed in fluid 12 of fluid storage tank 14. As shown in FIG. 1, probe 10 is a field device that includes submersible housing 16 and optional flexible transmission line 18 having ends 20 and 22. Submersible housing 16 connects to transmission line 18 at end 20 and houses electronic components, including one or more sensors for sensing parameters associated with fluid 12. Submersible housing 16 is resistant to fluid infiltration to protect the electronic components housed within it.

End 22 of transmission line 18 connects to process system 24, which may be a control room, another field device, or any other process control component or process control system known in the art. Transmission line 18 may serve various functions such as, for example, providing a communication link between probe 10 and process system 24, providing a means for supplying power to probe 10, providing a means for retrieving probe 10 from fluid 12, or any combination of these. In some embodiments, transmission line 18 includes an air channel for delivering compressed air to probe 10 (as described in greater detail below) to alter a density of probe 10.

For example, in one embodiment, transmission line 18 includes a process control loop such as a two-wire process control loop or a four-wire process control loop for providing power and a communication link to probe 10. Examples of suitable process control loop standards include the 4-20 mA standard, the HART® communication protocol, the FOUNDATION® Fieldbus communication protocol, the Profibus communication protocol, or any other process control loop standard known in the art.

When deployed in a fluid environment such as fluid storage tank 14, probe 10 can perform various functions. Probe 10 is adapted to produce an output, or series of outputs, representative of conditions associated with the fluid environment. In some embodiments, probe 10 can track its movement within the fluid environment and match sensor data to locations within the fluid environment. In addition, in some embodiments, probe 10 can affect its location within the fluid environment to sense parameters such as, for example, a depth of a fluid.

Figure 2:
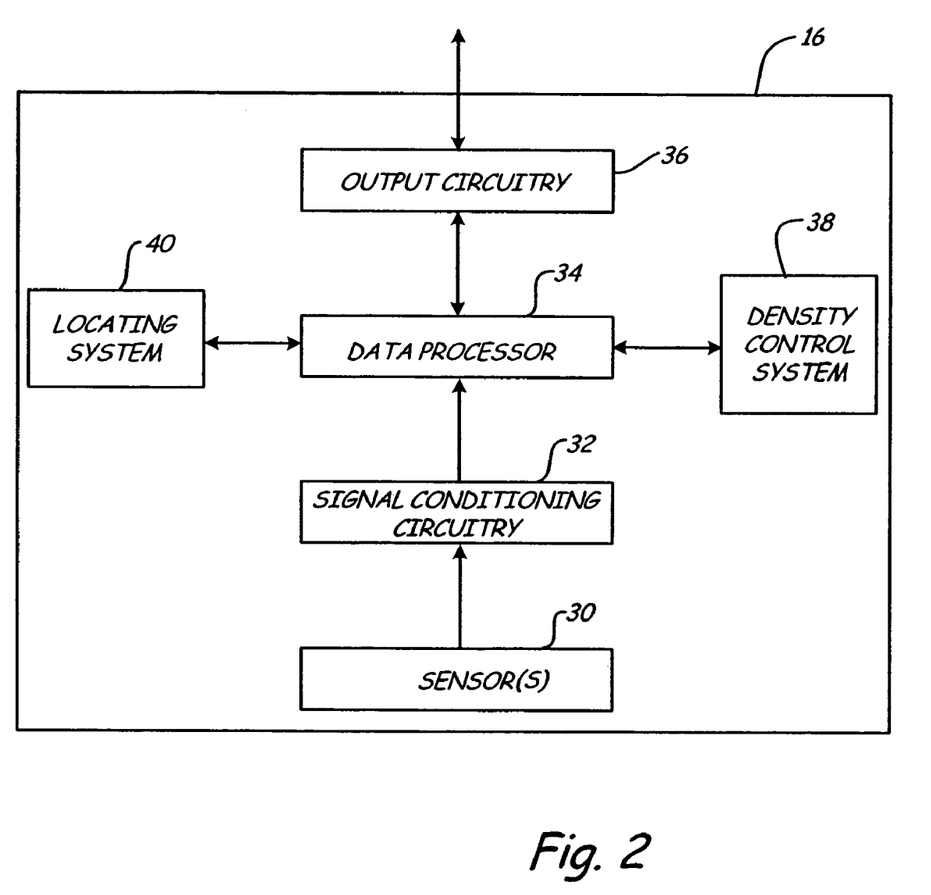
FIG. 2 is a block diagram of the submersible probe of FIG. 1.

FIG. 2 is a block diagram further illustrating probe 10 of FIG. 1. As shown in FIG. 2, probe 10 includes sensor(s) 30, signal conditioning circuitry 32, data processor 34, output circuitry 36, density control system 38, and locating system 40. Each sensor 30 measures a parameter associated with fluid 12 and produces a sensor signal representative of the sensed parameter. Signal processing circuitry 32 receives the sensor signal and conditions the sensor signal for use by data processor 34. Data processor 34 produces an output as a function of the conditioned sensor signal. Data processor 34 may then communicate the output to output circuitry 36 for transmittal to process system 24 via optional transmission line 18. In some embodiments, output circuitry 36 is wireless communication circuitry for wireless transmittal of information between probe 10 and process system 24.

Data processor 34 is also in communication with density control system 38 and locating system 40. Both density control system 38 and locating system 40 may include signal conditioning circuitry for conditioning signals for use by data processor 38.

Density control system 38, in conjunction with data processor 34, controls the overall density of probe 10 and can alter that overall density to affect the location of probe 10 in fluid 12. Examples of density control systems 38 include ballast systems that can expel and/or draw in fluid 12, inflatable chambers in communication with an internal or external pressurized air source, ballast weights releasably attached to submersible housing 16, and combinations of these. In some embodiments, transmission line 18 includes a channel communicating with ends 20 and 22 to deliver (or receive) pressurized air to one or more inflatable chamber associated with submersible housing 16. In one embodiment, density control system 38 includes ballast weights that are both releasably attached and tethered to submersible housing 16 so that density control system 38 can release the ballast weights to decrease the density of probe 10, while still allowing for recovery of the ballast weights via the tether.

Locating system 40, in conjunction with data processor 34, determines the location of probe 10 in fluid 12. Locating system 40 senses movements of probe 10 caused by density control system 38 (or any other factor) and communicates movement-related information to data processor 34, which computes the location of probe 10 in fluid 12 as a function of the movement-related information. Examples of locating systems 40 include linear accelerometers, angular accelerometers, any other inertial sensing system known in the art, gyroscopes, global positioning systems (GPS), and combinations of these. In an exemplary embodiment, locating system 40 includes a three-axis linear accelerometer that is provided with a stable reference frame to resist or compensate for rotational or twisting movements of probe 10. One method for providing a stable reference frame is to fix the accelerometer relative to submersible housing 16 and compute a stable reference frame using gyroscope measurements and/or angular accelerometer measurements.

Sensor(s) 30 can be any type of sensor capable of measuring temperature, pressure, flow, density, viscosity, pH, conductivity, product level, turbidity, vibration, position, analyte concentration, and any other chemical or physical property associated with fluid 12. In some embodiments, probe 10 includes a plurality of sensors 30 for sensing a plurality of parameters. Data processor 34 can match sensor data received from sensor(s) 30 to locational information received from locating system 40 to identify the location at which the sensor data was produced.

Figure 3:
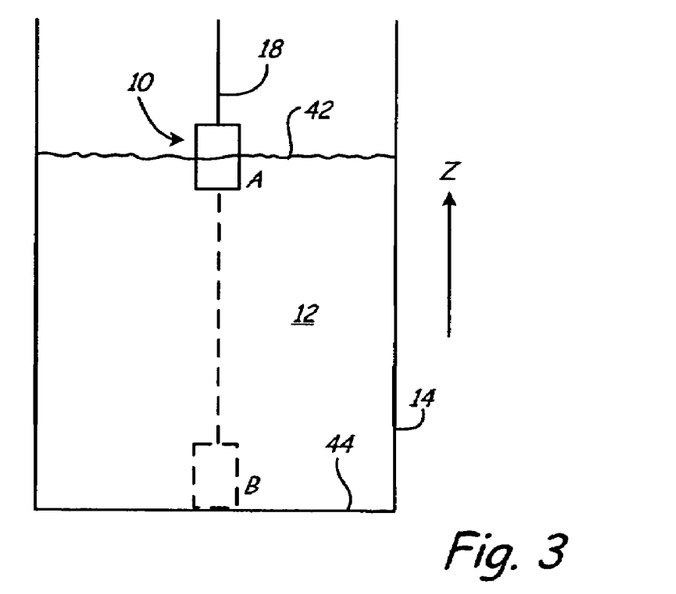
FIG. 3 illustrates one method of the present invention for determining a depth of a fluid using the probe of FIG. 1.
Figure 4:
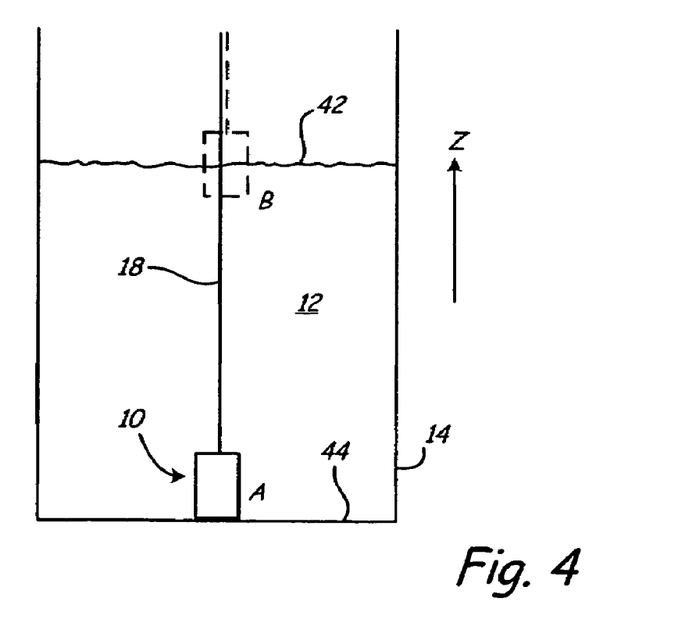
FIG. 4 illustrates another method of the present invention for determining a depth of a fluid using the probe of FIG. 1.

FIGS. 3 and 4 illustrate two different methods for using probe 10 to determine the depth of fluid 12 in fluid storage tank 14 relative to surface 42 and bottom 44. In both embodiments, locating system 40 of probe 10 includes an accelerometer capable of detecting acceleration in the vertical direction (i.e., in the direction of the z axis in FIGS. 3 and 4). In FIG. 3, the depth of fluid 12 is measured as probe 10 travels from surface 42 to bottom 44, whereas in FIG. 4, the depth of fluid 12 is measured as probe 10 travels from bottom 44 to surface 42.

As shown in FIG. 3, probe 10 is deployed at an initial location A of surface 42 so that probe 10 has a known initial velocity in the vertical direction. In most embodiments, this step involves locating probe 10 at surface 42 so that probe 10 has an initial velocity of about 0 meters per second (m/s) in the vertical direction. A 0 m/s initial velocity can be achieved, for example, by suspending probe 10 at surface 42 using transmission line 18 or by controlling the density of probe 10 so that it is buoyant in fluid 12.

Once probe 10 has a known initial velocity at surface 42, probe 10 is caused (or allowed) to descend toward bottom 44. If the density of probe 10, when deployed at location A, is less than that of fluid 12, the density of probe 10 is increased using density control system 38 so that probe 10 becomes more dense than fluid 12 and exhibits a negative buoyancy. Likewise, if transmission line 18 was tensioned to locate probe 10 at surface location A, that tension is relieved. While probe 10 descends, locating system 40 measures the instantaneous acceleration of probe 10 at a given time, t, and communicates the instantaneous acceleration to data processor 34, which computes the location of probe 10 at time t relative to location A as a function of the acceleration. When probe 10 comes to rest at location B of bottom 44, data processor 34 determines that probe 10 has stopped moving in the vertical direction. Data processor 34 then computes location B relative to location A and determines the vertical distance (or depth) between locations A and B.

In FIG. 4, the method of determining the vertical depth of fluid 12 is essentially the method of FIG. 3 executed in reverse. Probe 10 is deployed at initial location A on bottom 44, which is accomplished by controlling the density of probe 10 to be greater than that of fluid 12. Once probe 10 impacts bottom 44 and comes to rest at location A, the initial velocity in the vertical direction is known to be 0 m/s. Density system 38 then decreases the density of probe 10 until probe 10 is less dense than fluid 12 and exhibits a positive buoyancy. As probe 10 ascends towards surface 42, locating system 40 measures the instantaneous acceleration of probe 10 at a given time, t, and communicates the acceleration to data processor 34, which computes the location of probe 10 (relative to location A) at time t as a function of the acceleration. When probe 10 reaches location B of surface 42 and stops moving in the vertical direction, data process 34 computes location B relative to location A and determines the vertical distance between locations A and B.

In some embodiments, data processor 34 may continuously compute the position of probe 10 as it receives instantaneous acceleration data from locating system 40, while in other embodiments data processor 34 may store the instantaneous acceleration information for later computations of positions of probe 10 and/or depths of fluid 12. In some embodiments, data processor 34 can execute a volumetric algorithm to calculate the volume of fluid 12 stored in fluid storage tank 14. The algorithm produces the volume of fluid 12 stored in tank 14 as a function of the vertical depth of fluid 12 and dimensional information relating to fluid storage tank 14.

Figure 5A:
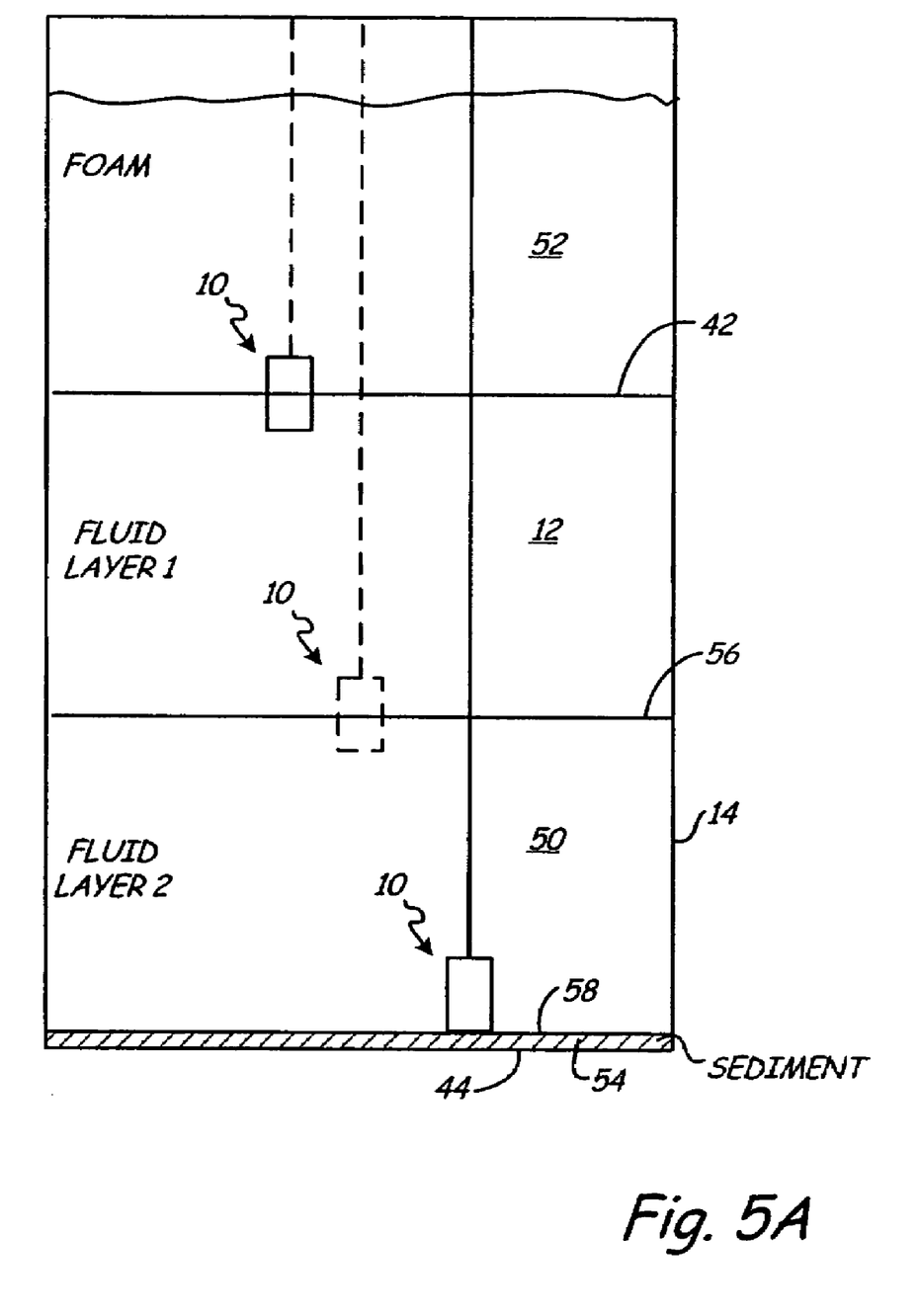
FIG. 5A illustrates a method of the present invention for determining depths of multiple fluid layers using the probe of FIG. 1.

FIG. 5A shows fluid storage tank 14 containing fluid 12, fluid 50, foam . 52, and sediment 54. Foam 52 covers surface 42 of fluid 12 and sediment 54 covers bottom 44 of fluid storage tank 14. Fluids 12 and 50 have different densities, with fluid 50 having a greater density than fluid 12. As shown in FIG. 5A, fluids 12 and 50 are immiscible, and form two layers that are separated from one another by interface 56.

Traditional depth measurement methods that use a float deployed on surface 42 cannot determine the individual depths of fluids 12 and 50 and may not be able to compensate for sediment 54. Likewise, traditional depth measurement methods using ultrasound sensors located above surface 42 may not yield reliable results due to the presence of foam 50 and/or sediment 54.

As shown in FIG. 5A, however, probe 10 can be used to determine the individual depths of fluids 12 and 50 by applying the methods of FIGS. 3 and 4. If the densities of fluids 12 and 50 are known, probe 10 can be deployed in fluid storage tank 14 so that its initial density is greater than the densities of fluids 12 and 50, thereby causing probe 10 to sink until reaching surface 58 of sediment 54. The density of probe 10 is then decreased to a density less dense than fluid 50 and more dense than fluid 12, causing probe 50 to ascend to interface 56. Using the methods described above for FIGS. 3 and 4, data processor 34 computes the depth of liquid 50 as a function of information collected by locating system 40 during the ascent from sediment 58 to interface 56. After coming to rest at interface 56, the density of probe 10 is again decreased so probe 10 becomes less dense than fluid 12, causing probe 10 to ascend to surface 42 and enabling probe 10 to compute the depth of fluid 12.

In situations where the densities of fluids 12 and 50 are not known or the number of interfaces 56 are not known, probe 10 can be used to determine the number of interfaces 56 present and the depth of each fluid layer separated by interfaces 56. For example, probe 10 can be deployed in fluid storage tank 14 so that probe 10 has either (a) a very high initial density to locate probe 10 at the bottom of storage tank 14 or (b) a very low initial density to locate probe 10 at surface 42. Depending upon which of these density strategies is employed, the density of probe 10 is then either gradually increased or decreased until vertical movement of probe 10 is detected by locating system 40. Once locating system 40 determines that all vertical movement of probe 10 has ceased (indicating that probe 10 has reached interface 56), the density of probe 10 is again gradually changed to re-initiate the ascent or descent. This process is repeated until probe 10 has reached a density upon which it is reasonable to conclude that probe 10 is located either at surface 42 or the bottom of storage tank 14.

Figure 5B:
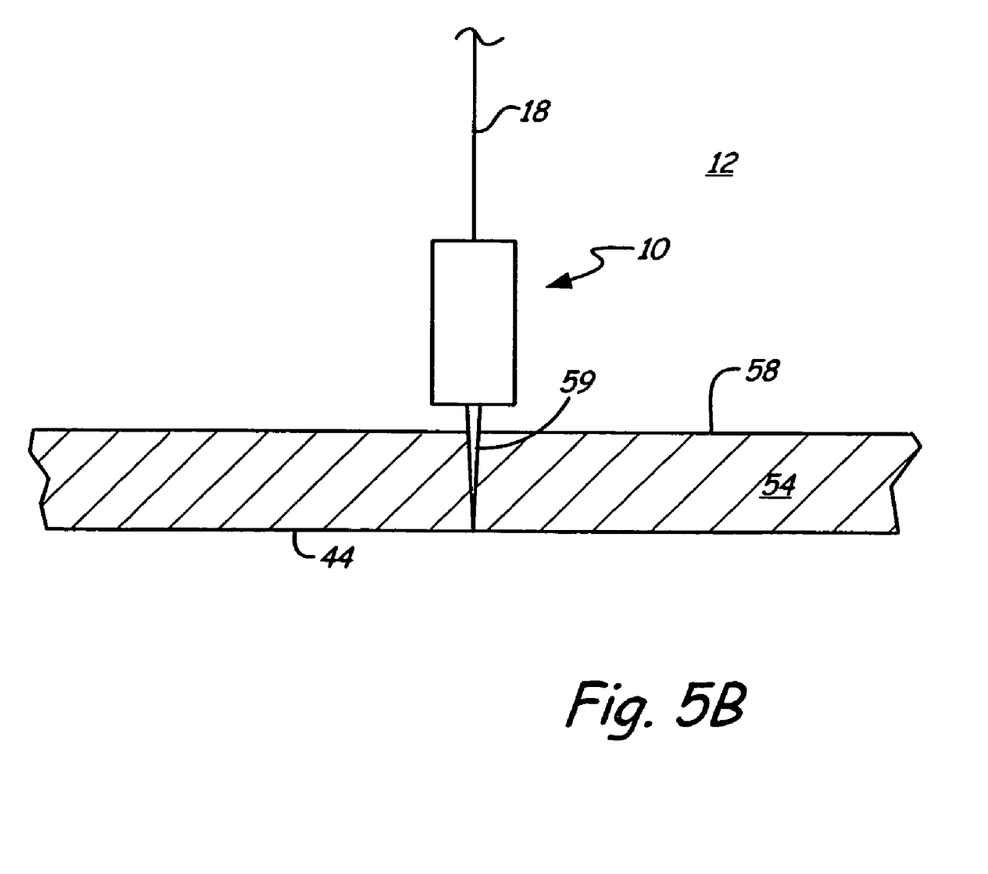
FIG. 5B depicts a submersible probe of the present invention equipped with a bottom-detect projection to pierce through a sediment.

In some embodiments, probe 10 can be used to compute a thickness of sediment 54. FIG. 5B shows probe 10 equipped with bottom-detect projection 59. As shown in FIG. 5B, projection 59 has a dagger-like shape to penetrate through sediment 54 and contact bottom 44. A probe 10 equipped with projection 59 can be used to compute a thickness of sediment 54 in the vertical direction. For example, probe 10 can first be deployed in fluid 12 without projection 59 and caused to sink and come into contact with surface 58 of sediment 54. Probe 10 can then be removed from fluid 12, equipped with projection 59, and caused to sink in fluid 12 such that projection 59 pierces through sediment 54 and contacts bottom 44. Data generated by locating system 40 can be used to determine the resting locations of probe 10 when equipped both with and without projection 59 and the vertical distance between surface 58 and bottom 44 can be computed to determine the thickness of sediment 54.

Although shown having a dagger-like shape in FIG. 5B, bottom-detect projection 59 can be of any shape capable of penetrating surface 58 of sediment 54. In some embodiments, the length of bottom-detect projection 59 is adjustable in the vertical direction to facilitate piercing through layers of sediment 54 of varying thicknesses.

Figure 6:
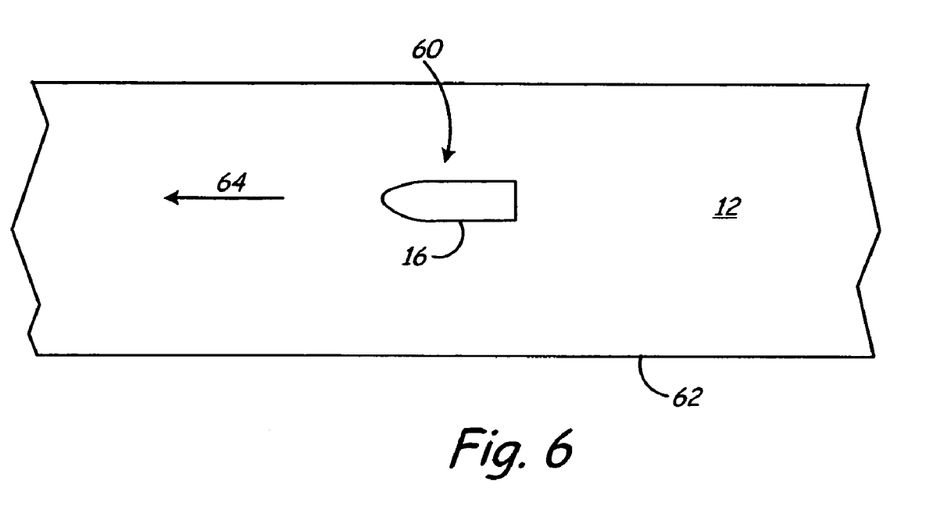
FIG. 6 depicts a submersible probe of the present invention deployed in a pipe system.

FIG. 6 shows submersible probe 60 of the present invention deployed in a pipe system 62 containing fluid 12 flowing in the direction of flow vector 64. In FIG. 5A, submersible housing 16 of probe 60 is bullet-shaped to facilitate movement of probe 60 through pipe system 62. The electronic components housed within submersible housing 16 are generally similar to those of FIG. 2, although, in some embodiments, probe 60 may not include density control system 38 or sensor(s) 30.

Locating system 40 of probe 60 includes a three-axis accelerometer capable of sensing accelerations of probe 60 in three dimensions, which enables probe 60 to track its three dimensional movement through pipe system 62. This movement information may be communicated to process system 24 via output circuitry 36 of FIG. 2 in the form of wireless communication circuitry. Alternatively, the movement information may be stored in memory contained within probe 60 for later access such as, for example, after recovery of probe 60 by a user at an outlet of pipe system 62. The movement information may be used, for example, to determine flow characteristics of fluid 12 in pipe system 62 and to identify blockages present within pipe system 62. Examples of pipe system 62 for use with probe 60 include sewer systems, water delivery systems, and petroleum pipe lines.

Submersible probes of the present invention may also be deployed in oceans, lakes, or rivers to study the physical, biological, and geological properties of the world's oceans and fresh-water bodies. For example, probe 10, when equipped with a three-axis accelerometer, may be deployed in an ocean to study parameters associated with various cold and warm water currents that exist within the world's oceans. In such situations, probe 10 can monitor the temperature of surrounding water using sensor(s) 30 and use density control system 38 to maintain the position of probe 10 relative to water with a specific temperature or an interface located between warm and cold water.

Any measurement, density-control, or other actions undertaken by the submersible probes of the present invention can occur either automatically or on a user-initiated basis. In addition, the position computations of the present invention can be performed by data processor 34 in real time as the instantaneous acceleration (or other movement parameter(s)) is being measured by locating system 40. Alternatively, the acceleration data may be stored and accessed at a later time for computational purposes by data processor 34 or process system 24.

As used herein, the term "data processor," includes any circuit or combination of circuits that can perform a logic or counting function to control the operation of field device 10 or carry out instructions or necessary steps to produce an output as a function of the condition sensor signals. Examples of data processors 34 include microprocessors, applications specific integrated circuits (ASICs), programmed gate arrays (PGAs), reduced instruction set computers, and any other suitable computation means known in the art. In one embodiment, data processor 34 is a microprocessor with associated memory.

In some embodiments, the submersible probes of the present invention are coated with a non-stick coating (such as, for example Teflon®) to discourage foreign material from accumulating on submersible housing 16. In some embodiments, submersible housing 16 is spherical to allow probe 10 to roll. The ability for probe 10 to roll may be useful for applications involving pipe system 62 or an irregular-shaped fluid storage tank 14. For example, when measuring the depth of fluid 12 in an irregular-shaped fluid storage tank 14, the ability to roll can encourage probe 10 to locate itself at the lowest point (i.e., the "true" bottom) of fluid storage tank 14.

Figure 7:
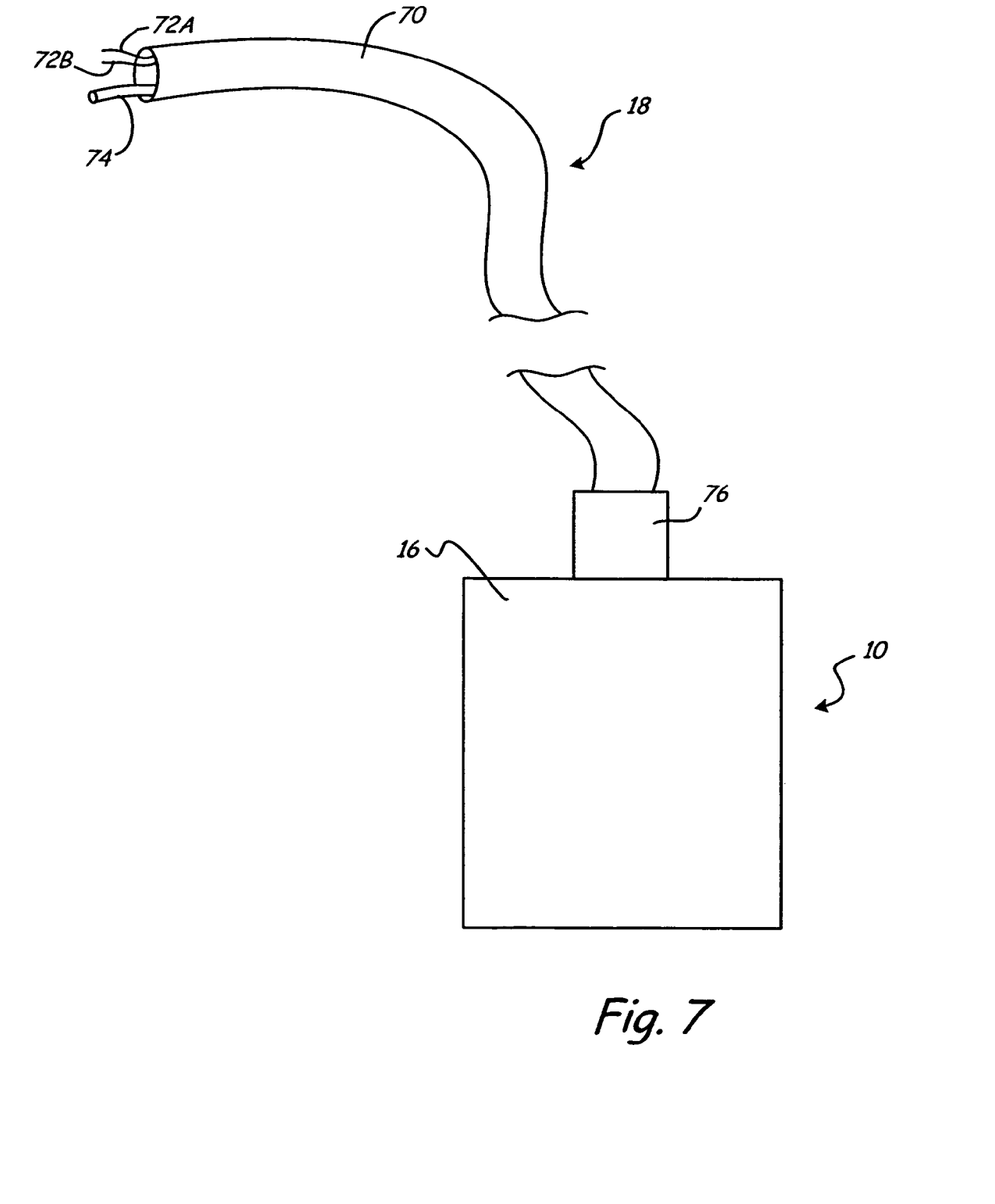
FIG. 7 is an embodiment of the submersible probe of FIG. 1 including a transmission line.

FIG. 7 shows submersible probe 10 of FIG. 1 equipped with one embodiment of transmission line 18. As shown in FIG. 7, transmission line 18 includes protective sheath 70, wires 72A and 72B, and air channel 74. Protective sheath 70 connects to housing 16 at end 20 via connector 76 and houses wires 72A and 72B and air channel 74. Wires 72A and 72B extend the length of protective sheath 70 and connect probe 10 to process system 24. In some embodiments, wires 72A and 72B comprise a two-wire process control loop. Air channel 74 also extends the length of protective sheath 70 and connects density control system 38 of FIG. 2 to an external air supply. In some embodiments, process system 24 of FIG. 1 includes an external air supply for altering a density of probe 10. In one embodiment, protective sheath 70 is configured to supply air directly from the external air supply to density control system 38 of FIG. 2, eliminating the need for air channel 74.

The supplied air can be used to change a density of probe 10 by displacing fluid that is either located within probe 10 or outside probe 10. In some embodiments, external fluid is displaced by inflating an expandable portion of housing 16 or transmission line 18. In one embodiment, fluid that is contained within an internal ballast system of probe 10 is displaced by the supplied air to change a density of probe 10.

Figure 8:
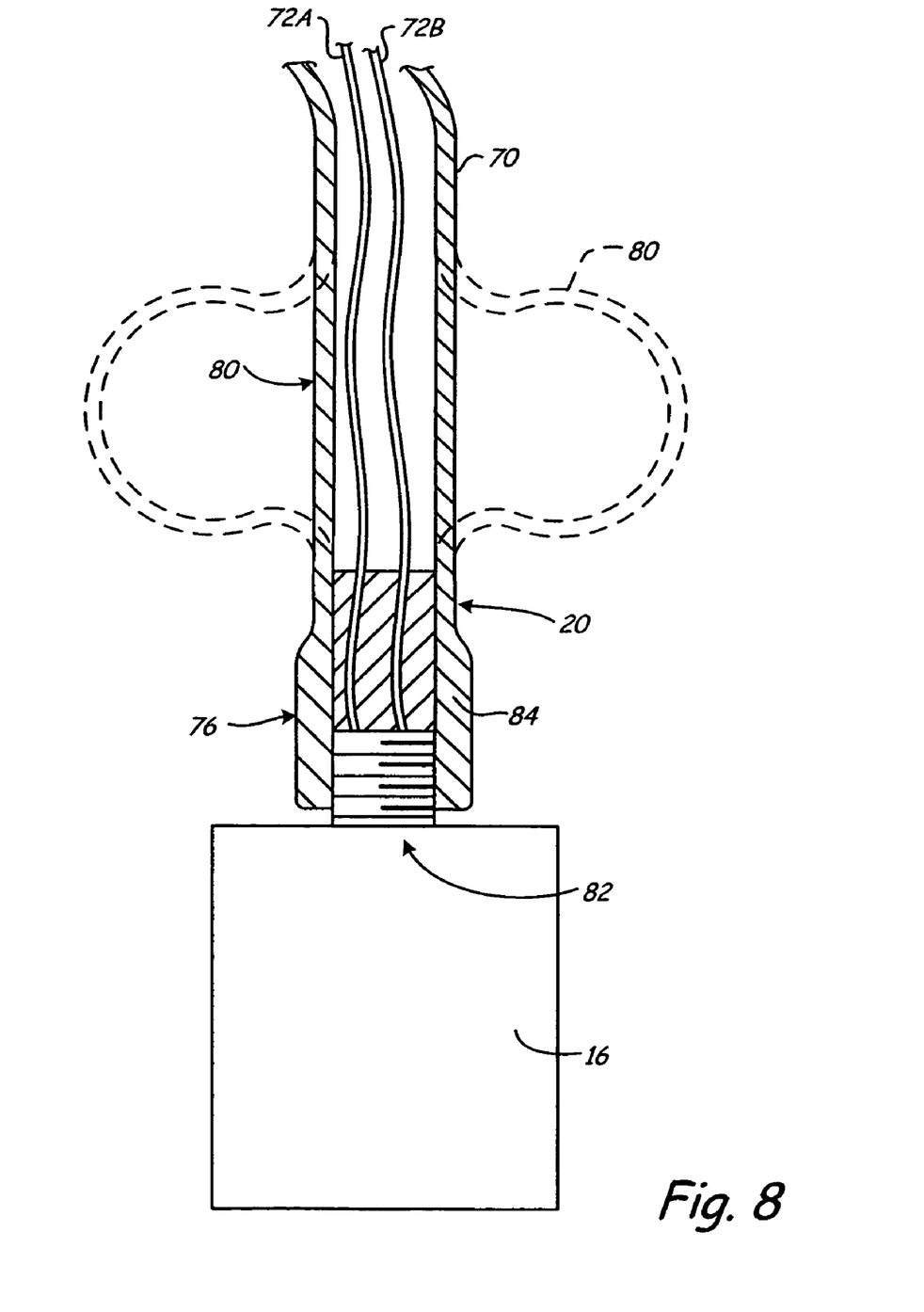
FIG. 8 is an embodiment of the submersible probe of FIG. 7 including an inflatable bladder.

FIG. 8 shows a cross-sectional view of transmission line 18 (without air channel 74) of submersible probe 10 of FIG. 7 equipped with an embodiment of density control system 38 including inflatable bladder 80. As shown in FIG. 8, inflatable bladder 80 comprises an expandable portion of sheath 70 that can be inflated by air supplied from an external air source via sheath 70 to control a density of probe 10. The broken lines illustrate an expanded condition of inflatable bladder 80 after inflation. In the embodiment of FIG. 8, housing 16 includes threaded collar 82 to mate with threads on connector 76 to connect end 20 of transmission line 18 and housing 16. Connector 76 includes seal 84 through which wired 72A and 72B pass. In some embodiments, transmission line 18 is secured to housing 16 via connector 76 in the form of a snap connector.

In some embodiments, inflatable bladder 70 is included in housing 16 instead of transmission line 18. For example, in some embodiments, inflatable bladder 70 comprises an expandable portion of housing 16.

FIGS. 9A-9C and FIGS. 10A-10D illustrate two embodiments of ballast systems for releasing ballast weight to control a density of probe 10. Any other ballast system known in the art can also be included in density control system 38 of probe 10.

Figure 9A:
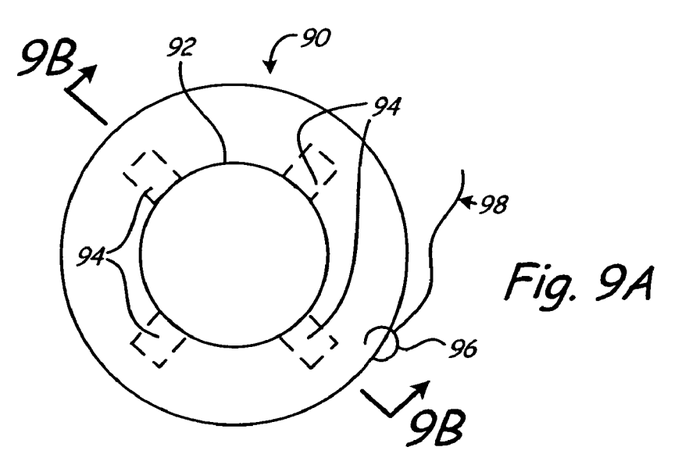
FIG. 9A is a top view of a releasable weight for use with an embodiment of the submersible probe of FIG. 1.
Figure 9B:
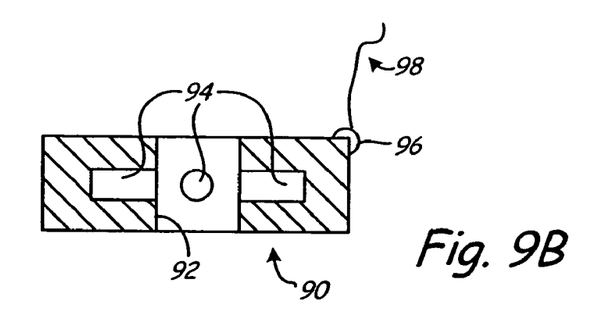
FIG. 9B is a cross-sectional side view of the releasable weight of FIG. 9A taken along line 9B of FIG. 9A.
Figure 9C:
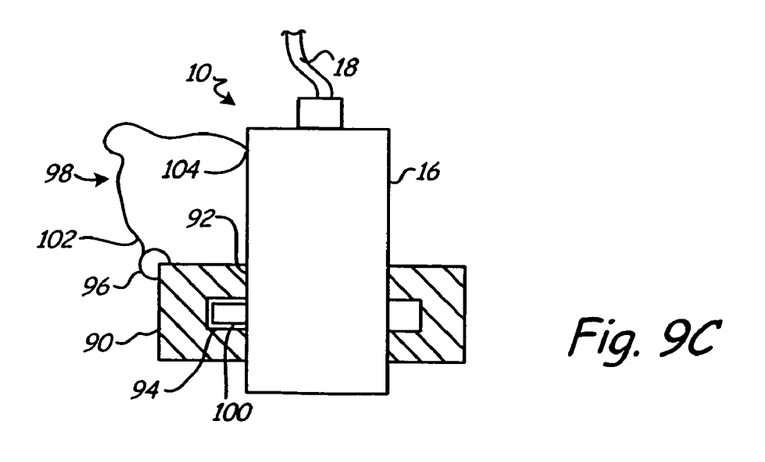
FIG. 9C is a cut-away view of the releasable weight of FIGS. 9A and 9B secured to an embodiment of the submersible probe of FIG. 1.

FIGS. 9A-9C show one embodiment of density control system 38 that includes releasable weight 90, with FIG. 9A showing a top view of releasable weight 90, FIG. 9B showing a cross-sectional side view taken along line 9B of FIG. 9A, and FIG. 9C showing a cut away view of releasable weight 90 mounted to housing 16 of probe 10. Weight 90 includes female mating surface 92, mounting recesses 94, tether mount 96, and tether 98. As shown in FIG. 9C, weight 90 can be secured to housing 16 by positioning housing 16 within female mating surface 92 so that one or more mounting recesses 94 can receive retractable mounting pin(s) 100 from housing 16. Weight 90 can subsequently be released from housing 16 by retracting mounting pin(s) 100. In some embodiments, multiple weights 90 can be secured to housing 16.

After release, weights 90 can be retrieved via tether 98, which as shown in FIG. 9C, attaches to weight 90 at first end 102 via tether mount 96 and attaches to housing 16 at second end 104. First end 102 can be attached to any suitable portion of weight 90 using any attachment or fastening means known in the art. Second end 104 can be attached to any suitable portion of housing 16, transmission line 18, or any other structure using any attachment or fastening means known in the art.

Figure 10A:
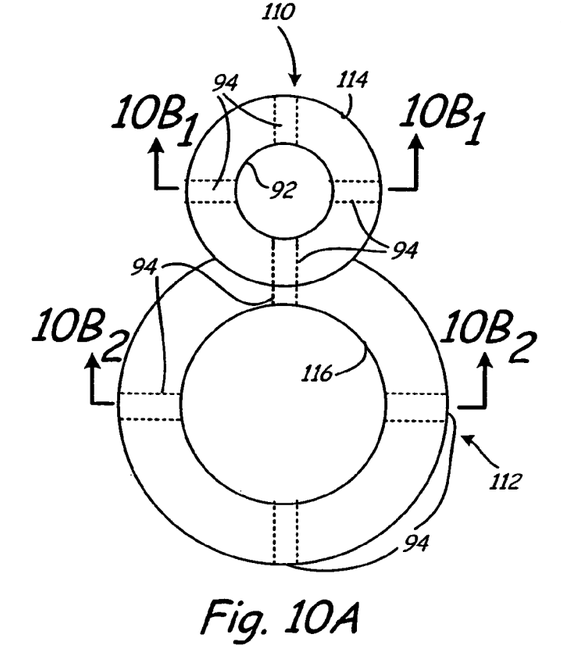
FIG. 10A is a top view of two releasable weights for use with an embodiment of the submersible probe of FIG. 1.
Figure 10B:
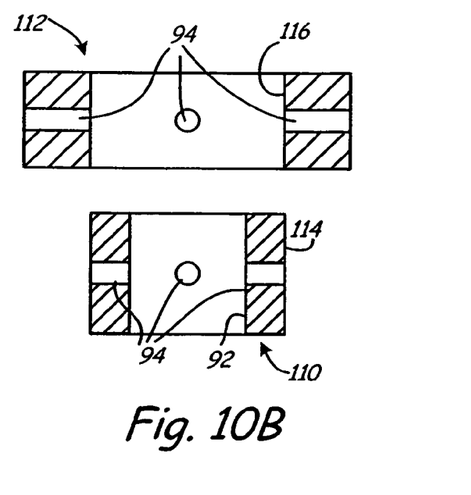
FIG. 10B is a cross-sectional side view of the releasable weights of FIG. 10A taken along lines $10B_1$ and $10B_2$ of FIG. 10A.
Figure 10C:
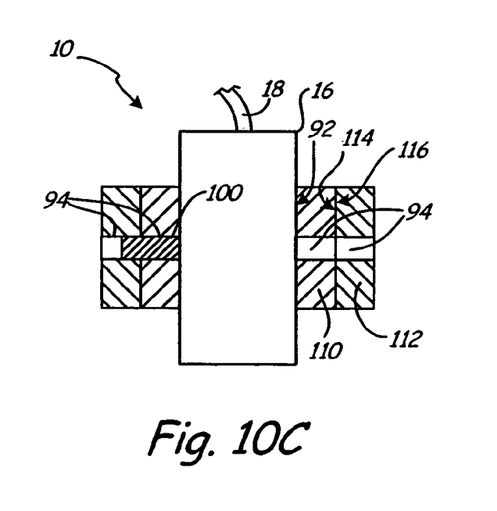
FIG. 10C is a cut-away view of the releasable weights of FIG. 10A secured to an embodiment of the submersible probe of FIG. 1.
Figure 10D:
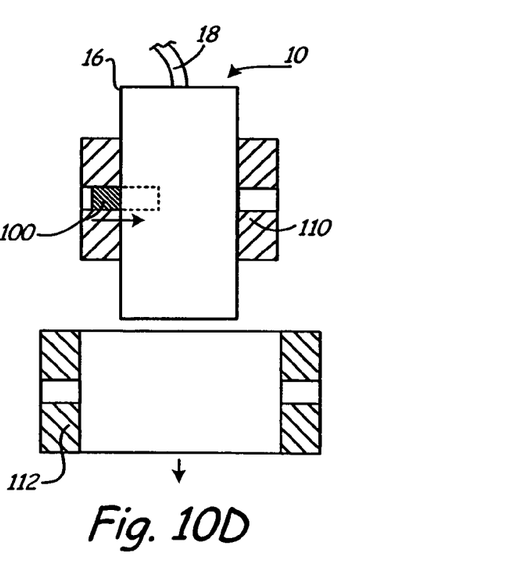
FIG. 10D shows one of the weights of FIG. 10C being released from the submersible probe of FIG. 10C.

FIGS. 10A-10D show an embodiment of density control system 38 of FIG. 2 that includes nested weights 110 and 112, with FIG. 10A showing a top view of weights 100 and 112, FIG. 10B showing a cross-sectional side view of weights 110 and 112 taken along lines $10B_1$ and $10B_2$, FIG. 10C showing a cut-away view of weights 110 and 112 secured to housing 16, and FIG. 10D showing weight 112 being released from housing 16. Similar to weight 90 of FIGS. 9A-9C, nested weights 110 and 112 include mounting recesses 94 for receiving retractable pins 100 from housing 16 of probe 10 and weight 110 includes female mating surface 112 for receiving housing 16. Weight 110 includes male surface 114, which is sized to mate with female surface 116 of weight 112 and allow weights 110 and 112 to be nested around housing 16 of probe 10 as shown in FIG. 10C.

Nested weights 110 and 112 can be secured by retractable pin(s) 100 of housing 16. As shown in FIG. 10D, retractable pin(s) 100 can be partially retracted to release weight 112. To release weight 110, retractable pin(s) 100 is fully retracted. The ballast system of FIGS. 10A-10D can be used, for example, in multilayer fluid applications such the one shown in FIG. 5A to determine a depth or volume of each fluid.

Thus, as described above, the submersible probe of the present invention provide an efficient means for measuring parameters associated with a fluid environment. The submersible probe may include a density system for altering a density of the probe to affect the location of the probe in the fluid environment. In addition, the submersible probe may also include a locating system for tracking the position of probe in the fluid environment.

Although the present invention has been described with reference to preferred embodiments, workers skilled in the art will recognize that changes may be made in form and detail without departing from the spirit and scope of the invention.

The invention claimed is:

1. A probe for deployment in a fluid and for producing an output representative of a parameter associated with the fluid, the probe comprising:
   a submersible housing;
   a sensor carried by the submersible housing to sense the parameter and produce a sensor signal representative of the parameter;
   a density control system carried by the submersible housing for altering a density of the probe while the probe is deployed in the fluid;
   a data processor in communication with the sensor to produce an output as a function of the sensor signal;
   output circuitry in communication with the data processor; and
   a flexible transmission line having a first and a second end, the first end connected to the submersible housing and in communication with the output circuitry and the second end for connecting to a remote process system, wherein the flexible transmission line is part of a process control loop.

2. The probe of claim 1, wherein the density control system comprises a ballast system.

3. The probe of claim 2, wherein the ballast system comprises releasable weights mounted to the submersible housing.

4. The probe of claim 3, wherein the weights are attached to a first end of a tether and the submersible housing is attached to a second end of the tether.

5. The probe of claim 1, wherein the density control system comprises an inflatable bladder.

6. The probe of claim 5, wherein a compressed air source is connected to the inflatable bladder.

7. The probe of claim 6, wherein the flexible transmission line includes an air channel to deliver compressed air from the first end of the transmission line to the inflatable bladder.

8. The probe of claim 1, wherein a plurality of sensors are carried by the submersible housing to sense a plurality of parameters.

9. The probe of claim 1, wherein the submersible housing is spherical.

10. The probe of claim 1, and further comprising:
a locating system in communication with the data processor.

11. The probe of claim 10, wherein the locating system comprises an accelerometer.

12. A probe for deployment in a fluid and for producing an output representative of a parameter associated with the fluid, the probe comprising:
a submersible housing;
a sensor carried by the submersible housing to sense the parameter and produce a sensor signal representative of the parameter;
a density control system carried by the submersible housing for altering a density of the probe while the probe is deployed in the fluid;
a data processor in communication with the sensor to produce an output as a function of the sensor signal;
output circuitry in communication with the data processor; and
a flexible transmission line having a first and a second end, the first end connected to the submersible housing and in communication with the output circuitry and the second end for connecting to a remote process system; and
a bottom-detect projection for piercing sediment located at a bottom of the fluid.

13. The probe of claim 1, wherein the sensor comprises an accelerometer.

14. A probe for deployment in a fluid and for producing an output representative of a parameter associated with the fluid, the probe comprising:
a submersible housing;
a sensor carried by the submersible housing to sense the parameter and produce a sensor signal representative of the parameter;
a density control system carried by the submersible housing for altering a density of the probe;
a data processor in communication with the sensor to produce an output as a function of the sensor signal;
output circuitry in communication with the data processor; and
a flexible transmission line having a first and a second end, the first end connected to the submersible housing and in communication with the output circuitry and the second end for connecting to a remote process system, wherein the flexible transmission line is part of a process control loop.

15. The probe of claim 14, wherein a plurality of sensors are carried by the submersible housing to sense a plurality of parameters.

16. The probe of claim 14, wherein the submersible housing is spherical.

17. The probe of claim 14, and further comprising:
a locating system in communication with the data processor.

18. The probe of claim 17, wherein the locating system comprises an accelerometer.

19. The probe of claim 14 and further comprising:
a bottom-detect projection for piercing sediment located at a bottom of the fluid.

20. A probe for deployment in a fluid and for producing an output representative of a plurality of parameters associated with the fluid, the probe comprising:
a submersible housing;
a plurality of sensors carried by the submersible housing to sense the plurality of parameters and produce sensor signals representative of the parameters;
a density control system carried by the submersible housing for altering a density of the probe;
a data processor in communication with the sensor to produce an output as a function of the sensor signal;
output circuitry in communication with the data processor;
a flexible transmission line having a first and a second end, the first end connected to the submersible housing and in communication with the output circuitry and the second end for connecting to a remote process system; and
a bottom-detect projection for piercing sediment located at a bottom of the fluid.

21. The probe of claim 20, wherein the submersible housing is spherical.

22. The probe of claim 20, wherein one of the plurality of sensors comprises an accelerometer.

23. A probe for deployment in fluid and for producing an output representative of a parameter associated with the fluid, the probe comprising:
a submersible housing;
a sensor carried by the submersible housing to sense the parameter and produce a sensor signal representative of the parameter;
a density control system carried by the submersible housing for altering a density of the probe;
a bottom-detect projection for piercing sediment located at the bottom of the fluids;
a data processor in communication with the sensor to produce an output as a function of the sensor signal;
output circuitry in communication with the data processor; and
a flexible transmission line having a first and a second end, the first end connected to the submersible housing and in communication with the output circuitry and the second end for connecting to a remote process system.

24. The probe of claim 23, wherein the density control system comprises a ballast system.

25. The probe of claim 23, wherein the density control system comprises an inflatable bladder.

* * * * *